(12) United States Patent
Nagai et al.

(10) Patent No.: US 8,273,837 B2
(45) Date of Patent: Sep. 25, 2012

(54) COMPOUND, POLYMER, AND RESIN COMPOSITION

(75) Inventors: Tomoki Nagai, Tokyo (JP); Takuma Ebata, Tokyo (JP); Nobuji Matsumura, Tokyo (JP)

(73) Assignee: JSR Corporation, Tokyo (JP)

(*) Notice: Subject to any disclaimer, the term of this patent is extended or adjusted under 35 U.S.C. 154(b) by 683 days.

(21) Appl. No.: 12/097,414

(22) PCT Filed: Dec. 13, 2006

(86) PCT No.: PCT/JP2006/324836
§ 371 (c)(1),
(2), (4) Date: Aug. 4, 2009

(87) PCT Pub. No.: WO2007/069640
PCT Pub. Date: Jun. 21, 2007

(65) Prior Publication Data
US 2009/0318652 A1    Dec. 24, 2009

(30) Foreign Application Priority Data
Dec. 14, 2005    (JP) ................................. 2005-360406

(51) Int. Cl.
*C08F 118/02* (2006.01)
(52) U.S. Cl. .......... 526/319; 560/25; 560/219; 560/221; 560/226; 560/222; 526/286; 526/289
(58) Field of Classification Search .................. 560/205, 560/219, 221, 226, 222; 526/286, 289
See application file for complete search history.

(56) References Cited

U.S. PATENT DOCUMENTS

| | | | |
|---|---|---|---|
| 4,477,640 A * | 10/1984 | Schmidt et al. | ............... 526/256 |
| 4,876,165 A | 10/1989 | Brewer et al. | |
| 4,910,122 A | 3/1990 | Arnold et al. | |
| 5,101,053 A | 3/1992 | Boettcher | |
| 5,130,392 A | 7/1992 | Schwalm et al. | |
| 5,674,648 A | 10/1997 | Brewer et al. | |
| 6,238,541 B1 | 5/2001 | Sasaki et al. | |

FOREIGN PATENT DOCUMENTS

| | | |
|---|---|---|
| DE | 3902114 | 8/1990 |
| EP | 0380010 | 8/1990 |
| JP | 2-264756 | 10/1990 |
| JP | 5-188598 | 7/1993 |
| JP | 6-12452 | 2/1994 |
| JP | 09-325497 | 12/1997 |
| JP | 10-221852 | 8/1998 |
| JP | 11-176727 | 7/1999 |
| JP | 11-279796 | 10/1999 |
| JP | 2002-145955 | 5/2002 |
| JP | 2002-201232 | 7/2002 |
| JP | 2005-84365 | 3/2005 |
| JP | 2006-259508 | 9/2006 |
| JP | 2006-259509 | 9/2006 |
| JP | 2006259509 A * | 9/2006 |

OTHER PUBLICATIONS

Baek et al; J. Microlith., Microfab., Microsyst. 4(1), 013002 (Jan.-Mar. 2005).*
Mizutani; English Translation of JP 2006259509 A; Sep. 2006.*
Mizutani; Abstract in English; JP 2006259509 A; Sep. 2006.*

* cited by examiner

*Primary Examiner* — Doris Lee
(74) *Attorney, Agent, or Firm* — Ditthavong Mori & Steiner, P.C.

(57) ABSTRACT

A radiation-sensitive resin composition which has high transparency to radiation, excelling in basic properties as a resist such as sensitivity, resolution, and pattern shape, and, in particular, exhibiting high resolution performance, excellent DOF and LER, and high resistance to a liquid medium used in liquid immersion lithography is provided. Also provided are a polymer which can be used in the composition, a novel compound useful for synthesizing the polymer, and a method of producing the composition. A radiation-sensitive resin composition having an excellent resistance to a liquid medium can be obtained by using the novel compound shown by the following formula (1),

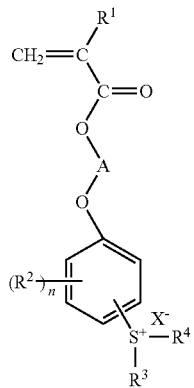

(1)

wherein $R^1$ represents a methyl group or a hydrogen atom, $R^2$, $R^3$ and $R^4$ individually represent a substituted or unsubstituted monovalent organic group having 1 to 10 carbon atoms, n is an integer from 0 to 3, A represents a methylene group, a linear or branched alkylene group having 2 to 10 carbon atoms, or an arylene group, and $X^-$ represents a counter ion of $S^+$.

5 Claims, 1 Drawing Sheet

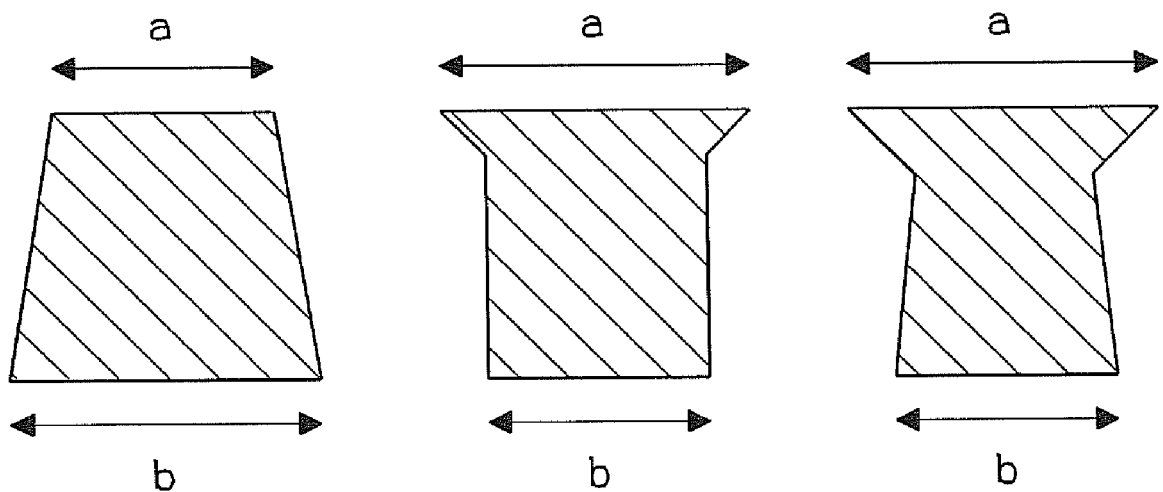

COMPOUND, POLYMER, AND RESIN COMPOSITION

TECHNICAL FIELD

The present invention relates to a novel compound, a polymer, and a radiation-sensitive resin composition or a radiation-sensitive resin composition used for liquid immersion lithography. In particular, the present invention relates to a radiation-sensitive resin composition suitably used as a chemically-amplified resist useful for microfabrication utilizing various types of radiation, for example, deep ultraviolet rays such as a KrF excimer laser or an ArF excimer laser, X-rays such as synchrotron radiation, or charged particle rays such as electron beams, and a radiation-sensitive resin composition for liquid immersion lithography used for forming an upper layer film of the resist, a polymer used in the resin compositions, a novel compound used as a monomer for synthesizing the polymer, and a method for producing the compositions.

BACKGROUND ART

In the field of microfabrication represented by the manufacture of integrated circuit elements, lithographic technology enabling microfabrication with a line width of about 200 nm or less using an ArF excimer laser (wavelength: 193 nm), an $F_2$ excimer laser (wavelength: 157 nm), and the like has been demanded in order to increase the degree of integration in recent years. As a radiation-sensitive resin composition applicable to excimer laser radiation, a number of chemically-amplified radiation-sensitive compositions utilizing a chemical amplification effect between a component having an acid-dissociable functional group and an acid generator which is a component generating an acid upon irradiation, have been proposed. For example, a high molecular-weight compound for a photoresist which comprises a resin component with a specific structure which contains a monomer unit having a norbornane ring derivative as a resin component is known (Patent Document 1 and Patent Document 2).

As a positive-tone photosensitive resin composition suitable for use with an exposure light source with a wavelength of 250 nm or less, particularly 220 nm or less, a resin in which an acid generating group, an alicyclic group, and an acid-dissociable group are introduced into the same molecule (Patent Document 3), a photosensitive resin composition containing a sulfonium or iodonium salt resin which has a counter anion in the polymer chain in order to increase photolysis efficiency (Patent Document 4), a positive-tone photosensitive resin composition having a counter anion in the polymer chain (Patent Document 5), and a negative-tone and positive-tone photosensitive resin composition of the same type (Patent Document 6) are known.

However, to achieve a higher degree of integration in the field of semiconductor devices, a radiation-sensitive resin composition used as a resist has been required to possess more excellent resolution. In addition, along with the progress of microfabrication, there is a growing demand for wider focal depth allowance (hereinafter referred to as "DOF") and narrower line edge roughness (hereinafter referred to as "LER") of patterns. Along with the progress of miniaturization in the semiconductor industry, development of a radiation-sensitive resin composition having excellent resolution and satisfying the demand for wide DOF and narrow LER is urgently needed.

In addition, the excellent characteristics such as sensitivity, resolution, DOF, and LER are desired to be maintained while such a radiation-sensitive resin composition is stored.

The resolution of the projection optical system provided in the projection aligner increases as the exposure wavelength used becomes shorter and the numerical aperture of the projection optical system becomes greater. Therefore, the exposure wavelength which is a wavelength of radiation used in the projection aligner has been reduced in accordance with scaling down of integrated circuits year by year, and the numerical aperture of the projection optical system has been increased.

Depth of focus is as important as resolution when carrying out the exposure. Resolution R and depth of focus δ are respectively shown by the following formulas, $$R = k1 \cdot \lambda / NA \qquad (i)$$

$$\delta = k2 \cdot \lambda / NA^2 \qquad (ii)$$

wherein λ is the exposure wavelength, NA is the numerical aperture of the projection optical system, and k1 and k2 are process coefficients. When obtaining the same resolution R, a larger depth of focus δ is obtained by using radiation with a shorter wavelength.

A photoresist film is formed on the surface of an exposure target wafer, and the pattern is transferred to the photoresist film. In a general projection aligner, the space in which the wafer is placed is filled with air or nitrogen. When the space between the wafer and the lens of the projection aligner is filled with a medium having a refractive index of n, the resolution R and the depth of focus δ are shown by the following formulas, $$R = k1 \cdot (\lambda/n) NA \qquad (iii)$$

$$\delta = k2 \cdot n \lambda / NA^2 \qquad (iv)$$

For example, when water is used as the above medium in a KrF process, the resolution R is 69.4% ($R = k1 \cdot (\lambda/1.44) NA$) and the depth of focus is 144% ($\delta = k2 \cdot 1.44 \lambda / NA^2$) in the case in which the photoresist is exposed through air or nitrogen, when the refractive index of light with a wavelength of 248 nm is n=1.44.

Such a projection exposure method to transfer more detailed patterns by reducing the wavelength of emitted light is called a liquid immersion lithographic method and is regarded as an essential technique for miniaturizing lithography, particularly lithography of the order of several tens of nanometers, and a projection aligner for the liquid immersion lithography is known (Patent Document 7).

In liquid immersion lithography, a photoresist film applied and formed on a wafer and a lens of the projection aligner respectively come into contact with an immersion medium such as water. The immersion medium may permeate into the photoresist film and reduce the photoresist resolution. Other problems are elution of a photoresist component into the immersion medium and pollution of the lens surface with such a photoresist component.

For these reasons, a photoresist film is demanded to maintain stability in the liquid immersion medium, that is, excellent liquid immersion resistance, without being eluted into an immersion medium such as water during liquid immersion lithography, and the exposed area thereof is required to be easily dissolved in an alkaline solution used as a developer.

However, no radiation-sensitive resin composition which can produce a stable film against an immersion medium such as water during liquid immersion lithography, while exhibiting excellent resolution has been obtained.

[Patent Document 1] JP-A-2002-201232
[Patent Document 2] JP-A-2002-145955
[Patent Document 3] JP-A-10-221852
[Patent Document 4] JP-A-9-325497
[Patent Document 5] JP-A-2005-84365
[Patent Document 6] U.S. Pat. No. 5,130,392
[Patent Document 7] JP-A-11-176727

DISCLOSURE OF THE INVENTION

Problems to be Solved by the Invention

The present invention provides a radiation-sensitive resin composition which has high transparency to radiation, excelling in basic properties as a resist such as sensitivity, resolution, and pattern shape, and, in particular, exhibiting high resolution performance, excellent DOF and LER, and high resistance to a liquid medium used in liquid immersion lithography. Also provided are a polymer which can be used in the composition, a novel compound useful for synthesizing the polymer, and a method of producing the composition.

Means for Solving the Problem

The composition of the present invention is shown by the following formula (1),

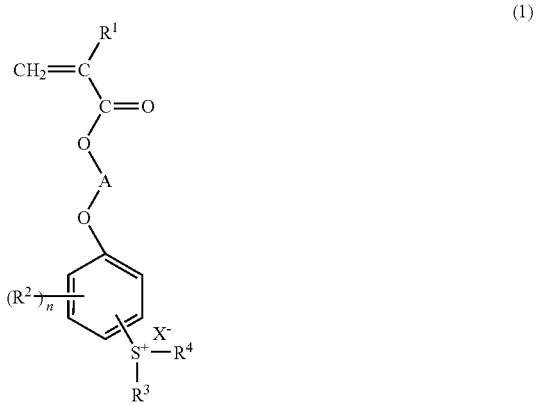

(1)

wherein $R^1$ represents a methyl group or a hydrogen atom, $R^2$, $R^3$ and $R^4$ individually represent a substituted or unsubstituted monovalent organic group having 1 to 10 carbon atoms, n is an integer from 0 to 3, A represents a methylene group, a linear or branched alkylene group having 2 to 10 carbon atoms, or an arylene group, and $X^-$ represents a counter ion of $S^+$.

The polymer of the present invention comprises a repeating unit derived from the compound shown by the formula (1) and has a polystyrene-reduced weight average molecular weight measured by gel permeation chromatography (GPC) of 1,000 to 100,000.

The polymer of the present invention further comprises a repeating unit having an acid-dissociable group.

The radiation-sensitive resin composition of the present invention comprises a resin containing an acid-dissociable group which is insoluble or scarcely-soluble in alkali and becomes alkali soluble by the action of an acid. The resin containing an acid-dissociable group is the polymer of the present invention.

The radiation-sensitive resin composition for liquid immersion lithography of the present invention is used in a system or a method of liquid immersion lithography which comprises irradiation through a liquid between a lens and a photoresist film. The resin component of the resin composition is the polymer of the present invention.

The method for producing the compound of the present invention shown by the formula (1) comprises reacting the compounds shown by the following formulas (1a) and (1b),

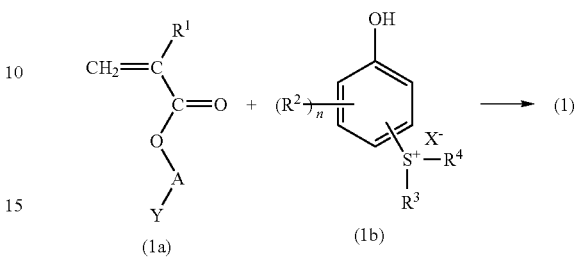

wherein $R^1$ represents a methyl group or a hydrogen atom, A represents a methylene group, a linear or branched alkylene group having 2 to 10 carbon atoms, or an arylene group, Y represents a halogen atom, $R^2$, $R^3$ and $R^4$ individually represent a substituted or unsubstituted monovalent organic group having 1 to 10 carbon atoms, n is an integer from 0 to 3, and $X^-$ represents a counter ion of $S^+$.

EFFECT OF THE INVENTION

The polymer, which is the resin component of the radiation-sensitive resin composition or the resin composition for forming an upper layer film, obtained by polymerizing the compounds shown by the formula (1), is caused to spread evenly over the polymer chains by irradiation, and generates an acid. Therefore, high resolution is achieved and DOF and LER can be improved by using the resin containing the acid generator of the present invention. In addition, since the composition is bonded by the specific group A in the formula (1), the storage stability of the compound or the resin improves.

BEST MODE FOR CARRYING OUT THE INVENTION

In the compound shown by the formula (1), A is a methylene group or a linear or branched alkylene group having 2 to 10 carbon atoms, and preferably an alkylene group having 2 to 10 carbon atoms or an arylene group. The etch resistance decreases if the number of carbon atoms exceeds 10.

As examples of the linear or branched alkylene group having 2 to 10 carbon atoms, an ethylene group, a propylene group such as a 1,3-propylene group and a 1,2-propylene group, a tetramethylene group, a pentamethylene group, a hexamethylene group, a heptamethylene group, an octamethylene group, a nonamethylene group, a decamethylene group, a 1-methyl-1,3-propylene group, a 2-methyl-1,3-propylene group, a 2-methyl-1,2-propylene group, a 1-methyl-1,4-butylene group, a 2-methyl-1,4-butylene group, and the like can be given. As examples of the arylene group, a phenylene group, a naphthylene group, an anthrylene group, a phenanthrylene group, and the like can be given. An alkylene group such as an ethylene group or a propylene group is preferable due to the excellent stability as a compound.

As examples of the substituted or unsubstituted monovalent organic group having 1 to 10 carbon atoms represented by $R^2$, $R^3$ and $R^4$, a linear or branched alkyl group, a linear or branched alkoxyl group, an aryl group, and the like can be given.

As examples of the linear or branched alkyl group, a methyl group, an ethyl group, an n-propyl group, an i-propyl group, an n-butyl group, a 2-methylpropyl group, a 1-methylpropyl group, a t-butyl group, a pentyl group, a hexyl group, a hydroxymethyl group, a hydroxyethyl group, and a trifluoromethyl group can be given.

A haloalkyl group obtained by replacing at least one hydrogen atom of these alkyl groups by a halogen atom can also be given as an example.

As examples of the linear or branched alkoxyl group, a methoxy group, an ethoxy group, an n-propoxy group, an i-propoxy group, an n-butoxy group, a 2-methylpropoxy group, a 1-methylpropoxy group, a t-butoxy group, an n-pentyloxy group, a neopentyloxy group, an n-hexyloxy group, an n-heptyloxy group, an n-octyloxy group, a 2-ethylhexyloxy group, an n-nonyloxy group, an n-decyloxy group, and the like can be given.

As examples of the aryl group, a phenyl group, a naphtyl group, and the like can be given.

As the above monovalent organic group, a phenyl group or a naphtyl group are preferable as $R^3$ and $R^4$ due to excellent stability of the compound shown by the formula (1).

As the monovalent organic group, $R^2$ is preferably an alkoxyl group such as a methoxy group, and n is preferably 0.

In the compound shown by the formula (1), $X^-$ is a sulfonate ion, a carboxylate ion, a halogen ion, a $BF^{4-}$ ion, a $PF^{6-}$ ion, or a tetraarylboronium ion.

As $X^-$, a sulfonate ion or a carboxylate ion having an alkyl group, an aryl group, an aralkyl group, an alicyclic alkyl group, a halogen-substituted alkyl group, a halogen-substituted aryl group, a halogen-substituted aralkyl group, an oxygen atom-substituted alicyclic alkyl group, or a halogen-substituted alicyclic alkyl group is preferable, with the preferable halogen as a substituent being a fluorine atom. The halogen ion as $X^-$ is preferably a chloride ion or a bromide ion, and the tetraarylboronium ion is preferably a $BPh^{4-}$ ion or a $B(C_6H_4(CF_3)_2)^{4-}$ ion.

Specific example of the preferable compound shown by the formula (1) is given below as the formula (1-1).

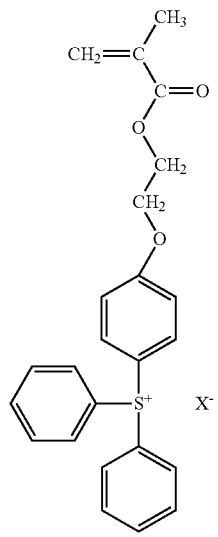

(1-1)

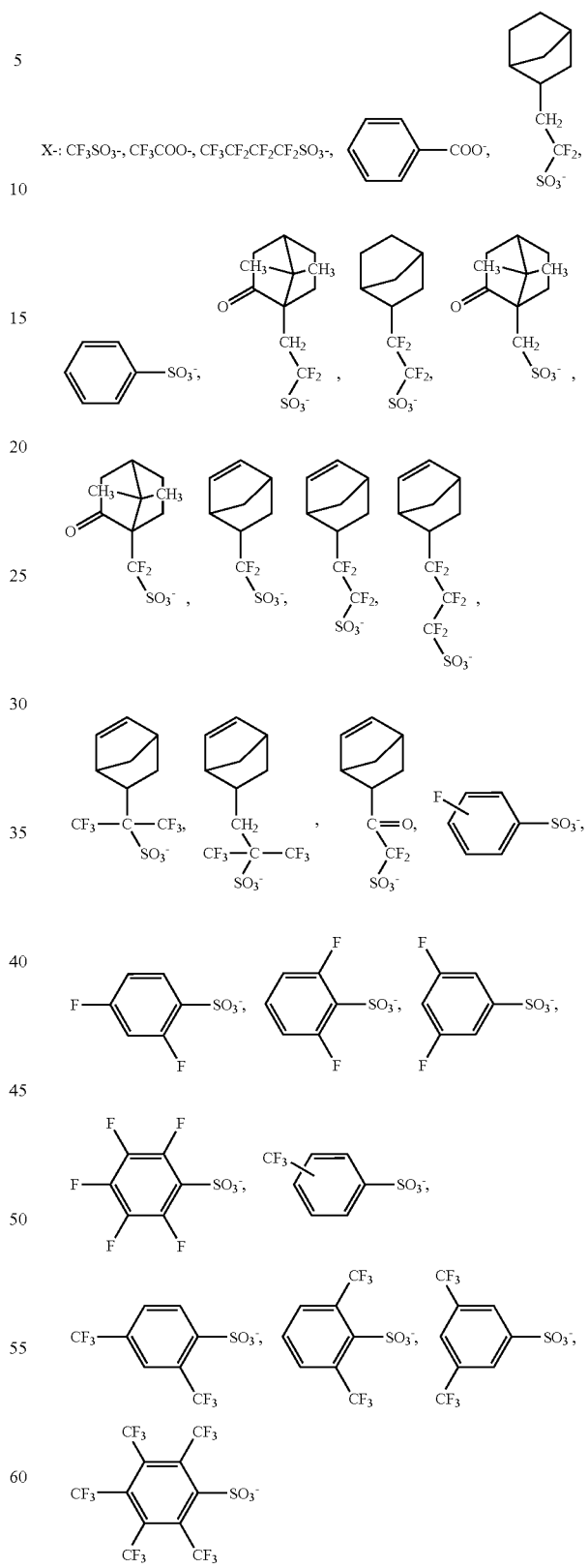

The compound shown by the formula (1) may be produced by the following method, for example.

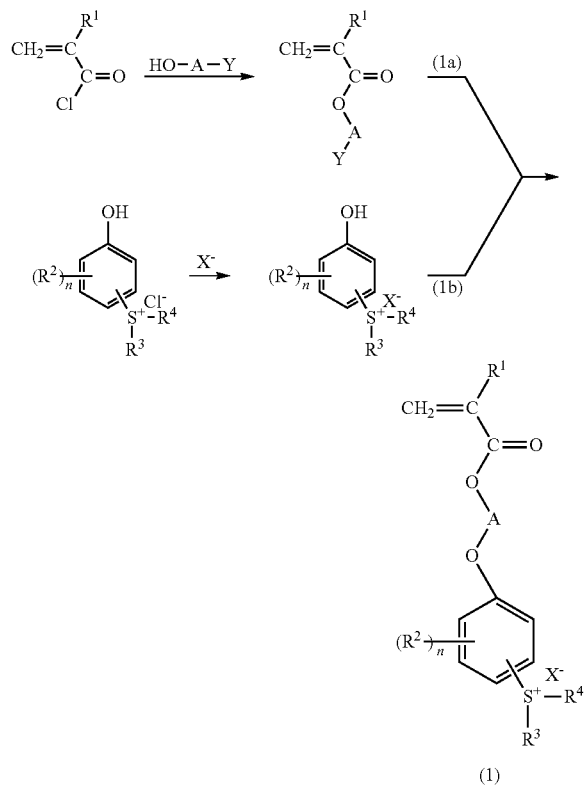

wherein A, $R^1$, $R^2$, $R^3$, $R^4$, and $X^-$ are the same as in the formula (1), and Y is a halogen atom.

The compound shown by the formula (1a) may be produced by reacting (meth)acrylic acid monochloride and a halogenated alcohol.

The compound shown by the formula (1b) may be produced by an ion-exchange reaction of a salt of an alkali metal or an alkali earth metal such as sodium sulfonate and lithium.

The obtained compound shown by the formula (1a) or (1b) is etherified according to the Williamson Synthesis to produce the compound shown by the formula (1).

The thus-obtained compound shown by the formula (1) may be purified by extraction with an organic solvent, column chromatography, or recrystallization.

As the organic solvent used in the purification, organic solvents which do not mix with water, such as esters (e.g. ethyl acetate, n-butyl acetate), ethers (e.g. diethyl ether), and halogenated alkyls (e.g. methylene chloride, chloroform) are preferable.

As the solvent used in the purification by column chromatography, a solvent mixed with an appropriate amount of an organic solvent such as methylene chloride, ethyl acetate or hexane is preferably used.

As the solvent used in the purification by recrystallization, a solvent mixed with an appropriate amount of an organic solvent such as methylene chloride, ethyl acetate, or hexane is preferably used.

The polymer of the present invention is obtained by polymerizing a monomer containing a compound shown by the formula (1) or copolymerizing monomers containing at least a compound shown by the formula (1) and a compound shown by the following formula (2),

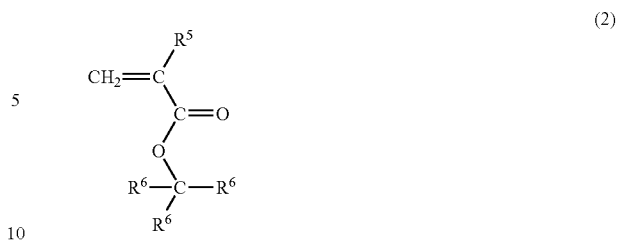

wherein $R^5$ represents a methyl group, a trifluoromethyl group, or a hydrogen atom, $R^6$ individually represents a monovalent alicyclic hydrocarbon group having 4 to 20 carbon atoms, a derivative thereof, or a linear or branched alkyl group having 1 to 4 carbon atoms, provided that at least one of the $R^6$ groups is an alicyclic hydrocarbon group or a derivative thereof, or two of the $R^6$ groups form a divalent alicyclic hydrocarbon group having 4 to 20 carbon atoms or a derivative thereof in combination with the carbon atom to which the two $R^6$ groups bond, with the remaining $R^6$ group being a linear or branched alkyl group having 1 to 4 carbon atoms, a monovalent alicyclic hydrocarbon group having 4 to 20 carbon atoms, or a derivative thereof.

As examples of the monovalent alicyclic hydrocarbon group having 4 to 20 carbon atoms and the divalent alicyclic hydrocarbon group having 4 to 20 carbon atoms formed by mutual bonding of two of the $R^6$ groups, a group having an alicyclic ring derived from cycloalkanes such as norbornane, tricyclodecane, tetracyclododecane, adamantane, cyclobutane, cyclopentane, cyclohexane, cycloheptane, and cyclooctane; a group obtained by substituting those groups having an alicyclic ring with at least one linear, branched or cyclic alkyl group having 1 to 4 carbon atoms such as a methyl group, an ethyl group, an n-propyl group, an i-propyl group, an n-butyl group, a 2-methylpropyl group, a 1-methylpropyl group, and a t-butyl group; and the like can be given. Among these alicyclic hydrocarbon groups, a group having an alicyclic ring derived from norbornane, tricyclodecane, tetracyclododecane, adamantane, cyclopentane, or cyclohexane and a group obtained by substituting those groups having an alicyclic ring with the above alkyl groups are preferable.

As examples of the substituent of the alicyclic hydrocarbon group, a group having one or more substituents such as a hydroxyl group; a carboxyl group; an oxo group (O group); a hydroxyalkyl group having 1 to 4 carbon atoms such as a hydroxymethyl group, a 1-hydroxyethyl group, a 2-hydroxyethyl group, a 1-hydroxypropyl group, a 2-hydroxypropyl group, a 3-hydroxypropyl group, a 1-hydroxybutyl group, a 2-hydroxybutyl group, a 3-hydroxybutyl group, and a 4-hydroxybutyl group; an alkoxyl group having 1 to 4 carbon atoms such as a methoxy group, an ethoxy group, an n-propoxy group, an i-propoxy group, an n-butoxy group, a 2-methylpropoxy group, a 1-methylpropoxy group, and a t-butoxy group; a cyano group; and a cyanoalkyl group having 2 to 5 carbon atoms such as a cyanomethyl group, a 2-cyanoethyl group, a 3-cyanopropyl group, and a 4-cyanobutyl group can be given. Of these substituents, a hydroxyl group, a carboxyl group, a hydroxymethyl group, a cyano group, a cyanomethyl group, and the like are preferable.

As examples of the linear or branched alkyl group having 1 to 4 carbon atoms represented by $R^6$, a methyl group, an ethyl group, an n-propyl group, an i-propyl group, an n-butyl group, a 2-methylpropyl group, a 1-methylpropyl group, and a t-butyl group can be given. Of these alkyl groups, a methyl group and an ethyl group are preferable.

—COOC(R⁶)₃ in the formula (2) is a part which dissociates by the action of an acid and produces a carboxyl group. As examples of the —C(R⁶)₃ part in —COOC(R⁶)₃, groups shown by the formulas (2a), (2b), (2c), and (2d) can be given.

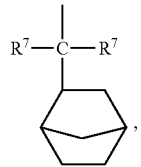
(2a)

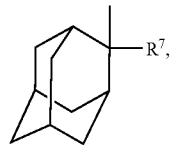
(2b)

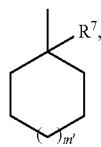
(2c)

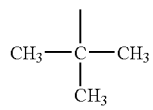
(2d)

wherein R⁷ individually represents a linear or branched alkyl group having 1 to 4 carbon atoms, and m' is 0 or 1.

As examples of the linear or branched alkyl group having 1 to 4 carbon atoms represented by R⁷, a methyl group, an ethyl group, an n-propyl group, an i-propyl group, an n-butyl group, a 2-methylpropyl group, a 1-methylpropyl group, and a t-butyl group can be given. Of these alkyl groups, a methyl group and an ethyl group are preferable.

As the group shown by the formula (2a), a group in which both of the R⁷s are a methyl group is particularly preferable. As the group shown by the formula (2b), a group in which the R⁷ is a methyl group or an ethyl group is particularly preferable. As the group shown by the formula (2c), a group in which the m' is 0 and the R⁷ is a methyl group, a group in which the m' is 0 and the R⁷ is an ethyl group, a group in which the m' is 1 and the R⁷ is a methyl group, or a group in which the m' is 1 and the R⁷ is an ethyl group is particularly preferable. In addition, a group shown by the formula (2a), (2b), or (2c) having a substituent is preferable.

Specific examples of the groups shown by the formula (2a), (2b), and (2c) are as follows.

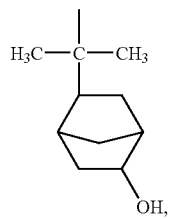 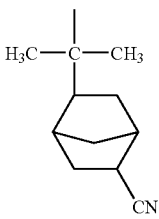 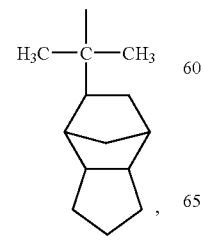

-continued

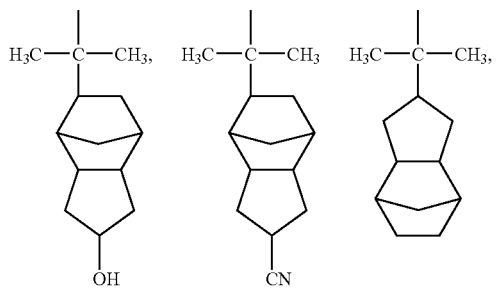

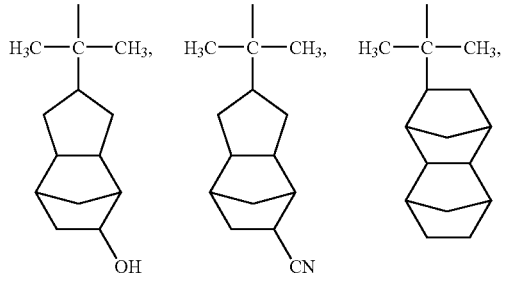

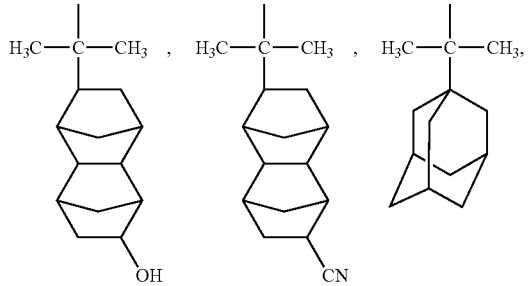

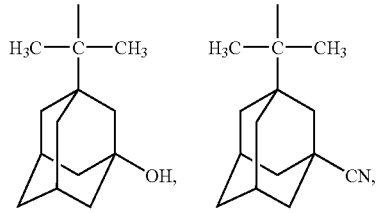

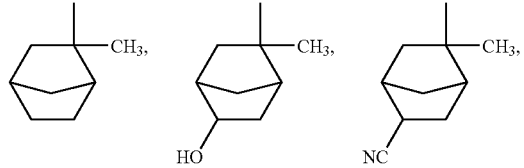

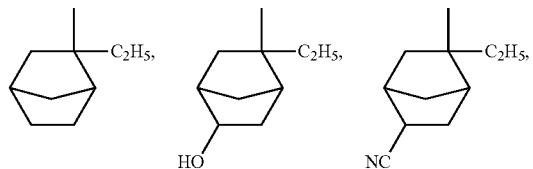

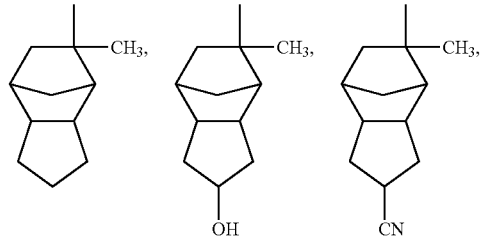

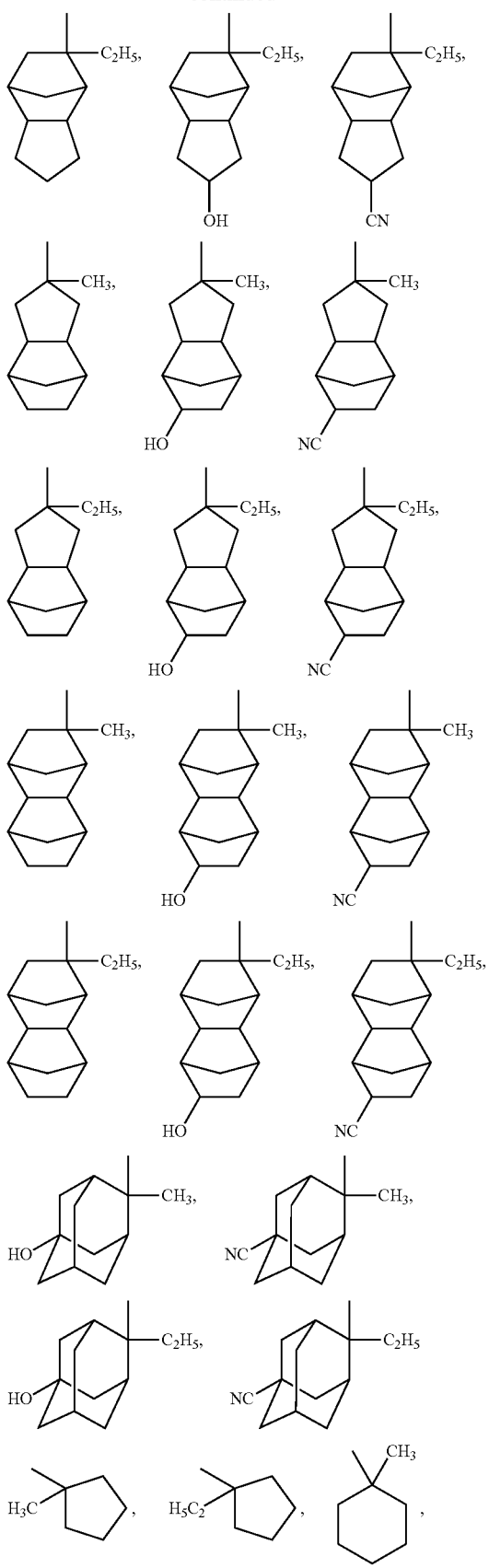

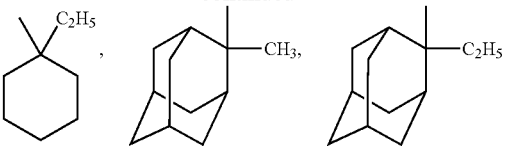

The polymer of the present invention may be copolymerized with the other compound as a monomer. The other compound preferably contains a compound shown by the following formula (3) as a monomer.

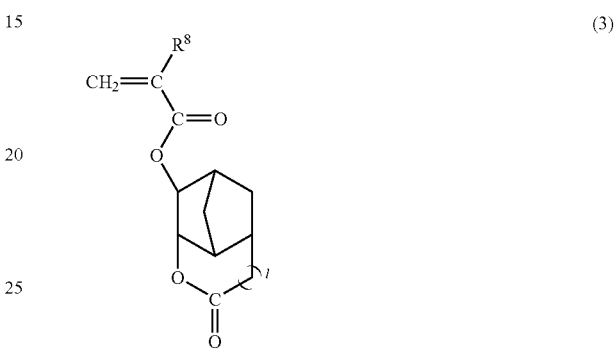

wherein $R^8$ represents a methyl group or a hydrogen atom, and l indicates 0 or 1.

Examples of the other compound include (meth)acrylates having a bridged hydrocarbon skeleton such as norbornyl (meth)acrylate, isobornyl (meth)acrylate, tricyclodecanyl (meth)acrylate, tetracyclodecanyl (meth)acrylate, dicyclopentenyl (meth)acrylate, adamantyl (meth)acrylate, and adamantylmethyl (meth)acrylate; carboxyl group-containing esters having a bridged hydrocarbon skeleton of an unsaturated carboxylic acid such as carboxynorbonyl (meth)acrylate, carboxytricyclodecanyl (meth)acrylate, and carboxytetracyclodecanyl (meth)acrylate; (meth)acrylates having no bridged hydrocarbon skeleton such as methyl (meth)acrylate, ethyl (meth)acrylate, n-propyl (meth)acrylate, n-butyl (meth)acrylate, 2-methylpropyl (meth)acrylate, 1-methylpropyl (meth)acrylate, t-butyl (meth)acrylate, 2-hydroxyethyl (meth)acrylate, 2-hydroxypropyl (meth)acrylate, 3-hydroxypropyl (meth)acrylate, cyclopropyl (meth)acrylate, cyclopentyl (meth)acrylate, cyclohexyl (meth)acrylate, 4-methoxycyclohexyl (meth)acrylate, 2-cyclopentyloxycarbonylethyl (meth)acrylate, 2-cyclohexyloxycarbonylethyl (meth)acrylate, and 2-(4-methoxycyclohexyl)oxycarbonylethyl (meth)acrylate; α-hydroxymethyl acrylates; unsaturated nitrile compounds; unsaturated amide compounds; nitrogen-containing vinyl compounds; unsaturated carboxylic acids (anhydrides) such as (meth)acrylic acid, crotonic acid, maleic acid, maleic acid anhydride, fumaric acid, itaconic acid, itaconic acid anhydride, citraconic acid, citraconic acid anhydride, and mesaconic acid; carboxyl group-containing esters having no bridged hydrocarbon skeleton of an unsaturated carboxylic acid such as 2-carboxyethyl (meth)acrylate, 2-carboxypropyl (meth)acrylate, 3-carboxypropyl (meth)acrylate, 4-carboxybutyl (meth)acrylate, and 4-carboxycyclohexyl (meth)acrylate; (meth)acryloyloxylactone compounds having an acid-dissociable group, monofunctional compounds such as a (meth)acryloyloxylactone compound which does not have an acid-dissociable group shown by the following formula (4);

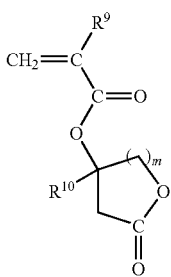

(4)

wherein $R^9$ represents a hydrogen atom, a methyl group, a trifluoromethyl group, or a hydroxymethyl group, $R^{10}$ individually represents a linear or branched alkyl group having 1 to 4 carbon atoms, and m is an integer of 1 or 2;

polyfunctional compounds having a bridged hydrocarbon skeleton such as 1,2-adamantanediol di(meth)acrylate, 1,3-adamantanediol di(meth)acrylate, 1,4-adamantanediol di(meth)acrylate, tricyclodecanyldimethylol di(meth)acrylate; and polyfunctional compounds having no bridged hydrocarbon skeleton.

Of these, (meth)acrylates having a bridged hydrocarbon skeleton are preferable.

The polymer of the present invention contains a compound shown by the formula (1) in an amount of 0.1 to 100 mol %, preferably 0.1 to 10 mol %, a compound shown by the formula (2) in an amount of 0 to 90 mol %, preferably 5 to 60 mol %, and a compound shown by the formula (3) in an amount of 0 to 70 mol %, preferably 20 to 60 mol % of the total amount of the compounds to be contained. The effect of the present invention is not exhibited if the amount of the compound shown by the formula (1) is less than 0.1 mol %. The adhesiveness with substrates decreases if the amount of the compound shown by the formula (2) exceeds 90 mol %. The resolution decreases if the amount of the compound shown by the formula (3) exceeds 70 mol %.

The polymer of the present invention may be prepared by polymerizing the above-mentioned compounds in an appropriate solvent in the presence of a chain transfer agent, as required, using a radical polymerization initiator such as hydroperoxides, dialkyl peroxides, diacyl peroxides, or an azo compound. As the solvent used for polymerization, alkanes such as n-pentane, n-hexane, n-heptane, n-octane, n-nonane, and n-decane; cycloalkanes such as cyclohexane, cycloheptane, cyclooctane, decalin, and norbornane; aromatic hydrocarbons such as benzene, toluene, xylene, ethylbenzene, and cumene; halogenated hydrocarbons such as chlorobutanes, bromohexanes, dichloroethanes, hexamethylene dibroinide, and chlorobenzene; saturated carboxylic acid esters such as ethyl acetate, n-butyl acetate, i-butyl acetate, and methyl propionate; ketones such as 2-butanone, 4-methyl-2-pentanone, and 2-heptanone; ethers such as tetrahydrofuran, dimethoxyethanes, and diethoxyethanes can be given. These solvents may be used either individually or in combination of two or more. The polymerization temperature is usually from 40 to 120° C., and preferably from 50 to 90° C. The reaction time is usually from 1 to 48 hours, and preferably from 1 to 24 hours.

The polymer of the present invention which contains a repeating unit having an acid-dissociable group may be used as a resin component of the radiation-sensitive resin composition which is insoluble or scarcely soluble in alkali and becomes easily soluble in alkali by the action of an acid. The polymer is also used as a resin component in the system or the method of liquid immersion lithography which comprises irradiation through a liquid between a lens and a photoresist film and in the resin composition for liquid immersion lithography used for forming an upper layer film covering the photoresist film.

The polystyrene-reduced weight average molecular weight of the polymer determined by gel permeation chromatography (GPC) (hereinafter referred to as "Mw") is usually 1,000 to 100,000, preferably 5,000 to 30,000, and more preferably 5,000 to 20,000 when used as the resin component of the radiation-sensitive resin composition. If the Mw of the polymer is less than 1,000, heat resistance as a resist may be decreased. If the Mw exceeds 100,000, developability as a resist may be decreased. The ratio of the Mw to the polystyrene-reduced number average molecular weight (hereinafter called "Mn") (Mw/Mn) determined by GPC of the polymer is usually 1 to 5, and preferably 1 to 3. It is preferable that the polymer contains almost no impurities such as halogens or metals. The smaller the amount of such impurities, the better the sensitivity, resolution, process stability, pattern shape, or the like as a resist. The polymer can be purified using, for example, a chemical purification method such as washing with water or liquid-liquid extraction or a combination of the chemical purification method and a physical purification method such as ultrafiltration or centrifugation. In the present invention, the polymer can be used either individually or in combination of two or more.

When the polymer is used as a resin component of the resin composition for liquid immersion lithography used for forming an upper layer film, Mw is preferably 2,000 to 100,000, more preferably 2,500 to 50,000, and even more preferably 3,000 to 20,000. If Mw of the polymer is less than 2,000, water resistance and mechanical properties of the upper layer film are unduly low; if more than 100,000, the solubility in the later-mentioned solvents is significantly low. The Mw/Mn ratio of the polymer is usually 1 to 5, and preferably 1 to 3.

In the radiation-sensitive resin composition of the present invention, a radiation-sensitive acid generator (hereinafter referred to as "acid generator") may be used in combination with the polymer shown by the formula (1). As examples of the acid generator, onium salt compounds, sulfonate compounds, and the like can be given. The following compounds can be given as examples of the acid generator.

(1) Onium Salt Compound:

As examples of the onium salt compounds, an iodonium salt, a sulfonium salt, a phosphonium salt, a diazonium salt, and a pyridinium salt can be given. As specific examples of the onium salt compounds, diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl.2-oxocyclohexyl.methylsulfonium trifluoromethanesulfonate, dicyclohexyl.2-oxocyclohexylsulfonium trifluoromethanesulfonate, 2-oxocyclohexyldimethylsulfonium trifluoromethanesulfonate, triphenylsulfonium nonafluoro-n-butanesulfonate, and the like can be given.

(2) Sulfonic Acid Compound:

As examples of the sulfonic acid compound, allyl sulfonates, alkylimide sulfonates, haloalkyl sulfonates, aryl sulfonates, and imino sulfonates can be given. As specific examples of the sulfonic acid compounds, benzointosylate, tris(trifluoromethanesulfonate) of pyrogallol, nitrobenzyl-9,10-diethoxyanthracene-2-sulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimidetrifluoromethanesulfonate, N-hydroxysuccinimidenonafluoro-n-butanesulfonate, N-hydroxysuccinimideperfluoro-n-octanesulfonate, 1,8-naphthalenedicarboxylic acid imide trifluoromethanesulfonate, 1,8-naphthalenedicarboxylic acid imide nonafluoro-n-butanesulfonate, 1,8-naphthalenedicarboxylic acid imide perfluoro-n-octanesulfonate, and the like can be given.

Among these acid generators, triphenylsulfonium nonafluoro-n-butanesulfonate, diphenyliodonium trifluoromethanesulfonate, diphenyliodonium nonafluoro-n-butanesulfonate, diphenyliodonium perfluoro-n-octanesulfonate, bis(4-t-butylphenyl)iodonium trifluoromethanesulfonate, bis(4-t-butylphenyl)iodonium nonafluoro-n-butanesulfonate, bis(4-t-butylphenyl)iodonium perfluoro-n-octanesulfonate, cyclohexyl.2-oxocyclohexyl.methylsulfonium trifluoromethanesulfonate, dicyclohexyl.2-oxocyclohexylsulfonium trifluoromethanesulfonate, 2-oxocyclohexyldimethylsulfonium trifluoromethanesulfonate, trifluoromethanesulfonylbicyclo[2.2.1]hept-5-ene-2,3-dicarbodiimide, nonafluoro-n-butanesulfonylbicyclo[2.2.1]hept-5-ene-2,3-dicarbodiimide, perfluoro-n-octanesulfonylbicyclo[2.2.1]hept-5-ene-2,3-dicarbodiimide, N-hydroxysuccinimidetrifluoromethanesulfonate, N-hydroxysuccinimidenonafluoro-n-butanesulfonate, N-hydroxysuccinimideperfluoro-n-octanesulfonate, 1,8-naphthalenedicarboxylic acid imide trifluoromethanesulfonate, and the like are preferable. These acid generators may be used either individually or in combination of two or more.

In the present invention, the total amount of the repeating unit derived from the compound of the formula (1) and the other acid generator contained in the polymer is usually 0.5 to 30 parts by weight, and preferably 1 to 25 parts by weight of 100 parts by weight of the resin in order to ensure sensitivity and developability of the resist. If the total amount is more than 30 parts by weight, a rectangular resist pattern may not be obtained due to decreased radiation transmittance. The proportion of the other acid generators to be added is usually 80 wt % or less, and preferably 60 wt % or less of the total amount of the acid generators used.

Various additives such as acid diffusion controllers, alicyclic additives having an acid-dissociable group, surfactants, and sensitizers can be optionally added to the radiation-sensitive resin composition of the present invention.

The acid diffusion controllers control diffusion of an acid generated from the acid generator upon exposure in the resist film to suppress undesirable chemical reactions in the unexposed area. The addition of such an acid diffusion controller improves storage stability of the resulting radiation-sensitive resin composition and resolution as a resist. Moreover, the addition of the acid diffusion controller prevents the line width of the resist pattern from changing due to changes in the post-exposure delay (PED) between exposure and post exposure heat treatment, whereby a composition with remarkably superior process stability can be obtained. As the acid diffusion controller, a nitrogen-containing organic compound which does not change its basicity by exposure and heat treatment during the process of resist pattern formation is preferable. As examples of the nitrogen-containing organic compounds, a compound shown by the following formula (5) (hereinafter called "nitrogen-containing compound (a)"), a compound having two nitrogen atoms in a molecule (hereinafter referred to as "nitrogen-containing compound (b)"); polyamino compounds and polymers having three or more nitrogen atoms in the molecule (hereinafter collectively referred to as "nitrogen-containing compound (c)"); amide group-containing compounds, and nitrogen-containing heterocyclic compounds can be given.

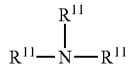

(5)

wherein $R^{11}$ individually represents a hydrogen atom, a substituted or unsubstituted, linear, branched, or cyclic alkyl group, a substituted or unsubstituted aryl group, or a substituted or unsubstituted aralkyl group.

As examples of the nitrogen-containing compound (a), mono(cyclo)alkylamines such as n-hexylamine, n-heptylamine, n-octylamine, n-nonylamine, n-decylamine, and cyclohexylamine; di(cyclo)alkylamines such as di-n-butylamine, di-n-pentylamine, di-n-hexylamine, di-n-heptylamine, di-n-octylamine, di-n-nonylamine, di-n-decylamine, cyclohexylmethylamine, and dicyclohexylamine; tri(cyclo)alkylamines such as triethylamine, tri-n-propylamine, tri-n-butylamine, tri-n-pentylamine, tri-n-hexylamine, tri-n-heptylamine, tri-n-octylamine, tri-n-nonylamine, tri-n-decylamine, cyclohexyldimethylamine, methyldicyclohexylamine, and tricyclohexylamine; aromatic amines such as aniline, N-methylaniline, N,N-dimethylaniline, 2-methylaniline, 3-methylaniline, 4-methylaniline, 4-nitroaniline, diphenylamine, triphenylamine, naphthylamine, and 2,6-diisopropylaniline; and the like can be given.

Examples of the preferable nitrogen-containing compounds (b) include ethylenediamine, N,N,N',N'-tetramethylethylenediamine, tetramethylenediamine, hexamethylenediamine, 4,4'-diaminodiphenylmethane, 4,4'-diaminodiphenyl ether, 4,4'-diaminobenzophenone, 4,4'-diaminodiphenylamine, 2,2-bis(4-aminophenyl)propane, 2-(3-aminophenyl)-2-(4-aminophenyl)propane, 2-(4-aminophenyl)-2-(3-hydroxyphenyl)propane, 2-(4-aminophenyl)-2-(4-hydroxyphenyl)propane, 1,4-bis[1-(4-aminophenyl)-1-methylethyl]benzene, 1,3-bis[1-(4-aminophenyl)-1-methylethyl]benzene, bis(2-dimethylaminoethyl)ether, and bis(2-diethylaminoethyl)ether. As examples of the nitrogen-containing compound (c), polyethyleneimine, polyallylamine, and a polymer of 2-dimethylaminoethylacrylamide can be given.

As examples of the amide group-containing compounds of the nitrogen group-containing compound (c), in addition to N-t-butoxycarbonyl group-containing amino compounds such as N-t-butoxycarbonyl di-n-octylamine, N-t-butoxycarbonyl di-n-nonylamine, N-t-butoxycarbonyl di-n-decylamine, N-t-butoxycarbonyl dicyclohexylamine, N-t-butoxycarbonyl-1-adamantylamine, N-t-butoxycarbonyl-N-methyl-1-adamantylamine, N,N-di-t-butoxycarbonyl-1-adamantylamine, N,N-di-t-butoxycarbonyl-N-methyl-1-adamantylamine, N-t-butoxycarbonyl-4,4'-diaminodiphenylmethane, N,N'-di-t-butoxycarbonylhexamethylenediamine, N,N,N'N'-tetra-t-butoxycarbonylhexamethylenediamine, N,N'-di-t-butoxycarbonyl-1,7-diaminoheptane, N,N'-di-t-butoxycarbonyl-1,8-diaminooctane, N,N'-di-t-butoxycarbonyl-1,9-diaminononane, N,N'-di-t-butoxycarbonyl-1,10-diaminodecane, N,N'-di-t-butoxycarbonyl-1,12-diaminododecane, N,N'-di-t-butoxycarbonyl-4,4'-diaminodiphenylmethane, N-t-butoxycarbonylbenzimidazole, N-t-butoxycarbonyl-2-methylbenzimidazole, and N-t-butoxycarbonyl-2-phenylbenzimidazole, formamide, N-methylformamide, N,N-dimethylformamide, acetamide, N-methylacetamide, N,N-dimethylacetamide, propionamide, benzamide, pyrrolidone, N-methylpyrrolidone, and the like can be given.

As examples of the nitrogen-containing heterocyclic compounds, 3-piperidino-1,2-propanediol and N-t-butoxycarbonyl-4-hydroxypiperidine can be given.

Of these nitrogen-containing organic compounds, the nitrogen-containing compound (a), the amide group-containing compound, and the nitrogen-containing heterocyclic compound are preferable. The acid diffusion controller may be used either individually or in combination of two or more.

The alicyclic additives having the above acid-dissociable group further improve dry etching resistance, pattern shape, and adhesion to the substrate. As examples of the alicyclic additives, adamantane derivatives such as t-butyl-1-adamantane carboxylate, t-butoxycarbonylmethyl-1-adamantane carboxylate, di-t-butyl-1,3-adamantane dicarboxylate, t-butyl-1-adamantane acetate, t-butoxycarbonylmethyl-1-adamantane acetate, and di-t-butyl-1,3-adamantane diacetate; deoxycholates such as t-butyl-deoxycholate, t-butoxycarbonylmethyl deoxycholate, 2-ethoxyethyl deoxycholate, 2-cyclohexyloxyethyl deoxycholate, 3-oxocyclohexyl deoxycholate, tetrahydropyranyl deoxycholate, and mevalonolactone deoxycholate; lithocholates such as t-butyl lithocholate, t-butoxycarbonylmethyl lithocholate, 2-ethoxyethyl lithocholate, 2-cyclohexyloxyethyl lithocholate, 3-oxocyclohexyl lithocholate, tetrahydropyranyl lithocholate, mevalonolactone lithocholate; and the like can be given. These alicyclic additives may be used either individually or in combination of two or more.

The surfactant improves applicability, striation, developability, and the like of the radiation-sensitive resin composition. As examples of the surfactant, nonionic surfactants such as polyoxyethylene lauryl ether, polyoxyethylene stearyl ether, polyoxyethylene oleyl ether, polyoxyethylene n-octyl phenyl ether, polyoxyethylene n-nonyl phenyl ether, polyethylene glycol dilaurate, and polyethylene glycol distearate; and commercially available products such as "KP341" (manufactured by Shin-Etsu Chemical Co., Ltd.), "POLYFLOW No. 75" and "POLYFLOW No. 95" (manufactured by Kyoeisha Chemical Co., Ltd.), "FTOP EF301", "FTOP EF303", and "FTOP EF352" (manufactured by Tohkem Products Corp.), "MEGAFAC F171" and "MEGAFAC F173" (manufactured by Dainippon Ink and Chemicals, Inc.), "Fluorad FC430" and "Fluorad FC431" (manufactured by Sumitomo 3M Ltd.), "Asahi Guard AG710" and "Surflon S-382", "Surflon SC-101", "Surflon SC-102", "Surflon SC-103", "Surflon SC-104", "Surflon SC-105", and "Surflon SC-106" (manufactured by Asahi Glass Co., Ltd.) can be given. These surfactants may be used either individually or in combination of two or more.

As other additives, alkali-soluble resins, low molecular weight alkali solubility controllers containing an acid-dissociable protective group, halation inhibitors, storage stabilizers, antifoaming agents, and the like can be given.

The radiation-sensitive resin composition of the present invention is prepared as a composition solution by being dissolved in a solvent in an amount to make a total solid content of usually 5 to 50 wt %, and preferably 10 to 25 wt %, and purified by a filter having a pore diameter of approximately 0.2 μm.

Examples of the solvent used for preparing the radiation-sensitive resin composition solution of the present invention include linear or branched ketones such as 2-butanone, 2-pentanone, 3-methyl-2-butanone, 2-hexanone, 4-methyl-2-pentanone, 3-methyl-2-pentanone, 3,3-dimethyl-2-butanone, 2-heptanone, and 2-octanone; cyclic ketones such as cyclopentanone, 3-methylcyclopentanone, cyclohexanone, 2-methylcyclohexanone, 2,6-dimethylcyclohexanone, and isophorone; propylene glycol monoalkyl ether acetates such as propylene glycol monomethyl ether acetate, propylene glycol monoethyl ether acetate, propylene glycol mono-n-propyl ether acetate, propylene glycol mono-i-propyl ether acetate, propylene glycol mono-n-butyl ether acetate, propylene glycol mono-i-butyl ether acetate, propylene glycol mono-sec-butyl ether acetate, and propylene glycol mono-t-butyl ether acetate; alkyl-2-hydroxypropionates such as methyl-2-hydroxypropionate, ethyl-2-hydroxypropionate, n-propyl-2-hydroxypropionate, i-propyl-2-hydroxypropionate, n-butyl-2-hydroxypropionate, i-butyl-2-hydroxypropionate, sec-butyl-2-hydroxypropionate, and t-butyl-2-hydroxypropionate; alkyl-3-alkoxypropionates such as methyl-3-methoxypropionate, ethyl-3-methoxypropionate, methyl-3-ethoxypropionate, and ethyl-3-ethoxypropionate; as well as n-propyl alcohol, i-propyl alcohol, n-butyl alcohol, t-butyl alcohol, cyclohexanol, ethylene glycol monomethyl ether, ethylene glycol monoethyl ether, ethylene glycol mono-n-propyl ether, ethylene glycol mono-n-butyl ether, diethylene glycol dimethyl ether, diethylene glycol diethyl ether, diethylene glycol di-n-propyl ether, diethylene glycol di-n-butyl ether, ethylene glycol monomethyl ether acetate, ethylene glycol monoethyl ether acetate, ethylene glycol mono-n-propyl ether acetate, propylene glycol monomethyl ether, propylene glycol monoethyl ether, propylene glycol mono-n-propyl ether, toluene, xylene, ethyl 2-hydroxy-2-methyl propionate, ethoxyethyl acetate, ethyl hydroxyacetate, methyl 2-hydroxy-3-methylbutyrate, 3-methoxybutylacetate, 3-methyl-3-methoxybutylacetate, 3-methyl-3-methoxybutylpropionate, 3-methyl-3-methoxybutylbutyrate, ethyl acetate, n-propyl acetate, n-butyl acetate, methyl acetoacetate, ethyl acetoacetate, methyl pyruvate, ethyl pyruvate, N-methylpyrrolidone, N,N-dimethylformamide, N,N-dimethylacetamide, benzyl ethyl ether, di-n-hexyl ether, diethylene glycol monomethyl ether, diethylene glycol monoethyl ether, caproic acid, caprylic acid, 1-octanol, 1-nonanol, benzyl alcohol, benzyl acetate, ethyl benzoate, diethyl oxalate, diethyl maleate, γ-butyrolactone, ethylene carbonate, and propylene carbonate.

These solvents may be used individually or in combination of two or more. Among these solvents, linear or branched ketones, cyclic ketones, propylene glycol monoalkyl ether acetates, alkyl 2-hydroxypropionates, and alkyl 3-alkoxypropionates are preferable.

The radiation-sensitive resin composition of the present invention is particularly useful as a chemically-amplified resist. In the present invention, the acid-dissociable group in the resin dissociates by the action of the acid generated from the acid generating component in the resin or the acid generator by exposure to radiation and produces a carboxyl group. The acid increases the solubility of the resist in the irradiated part in an alkaline developer to the extent that the irradiated part is dissolved and removed by an alkaline developer to produce a positive tone resist pattern.

A resist pattern is formed from the radiation-sensitive resin composition of the present invention by applying the composition solution to, for example, substrates such as a silicon wafer or a wafer coated with aluminum using an appropriate application method such as rotational coating, cast coating, and roll coating to form a resist film. The resist film is then optionally pre-baked (hereinafter called "PB") and exposed to radiation to form a specific resist pattern. For the radiation, visible rays, ultraviolet rays, deep ultraviolet rays, X-rays, electron beams, and the like can be appropriately selected according to the type of acid generator. Of these, the deep ultraviolet rays such as an ArF excimer laser (wavelength: 193 nm) and a KrF excimer laser (wavelength: 248 nm) are preferable. The ArF excimer laser (wavelength: 193 nm) is particularly preferable. In the present invention, it is preferable to perform post-exposure bake (hereinafter called "PEB"). The PEB ensures smooth dissociation of the acid-dissociable group in the resin (A). The heating temperature for the PEB is usually 30 to 200° C., and preferably 50 to 170° C., although the heating conditions are changed according to the composition of the radiation-sensitive resin composition.

In order to bring out the maximum potential of the radiation-sensitive resin composition of the present invention, an organic or inorganic anti-reflection film may be formed on a substrate as disclosed in JP-B-6-12452, for example. Moreover, a protective film may be formed on the resist film as disclosed in JP-A-5-188598, for example, in order to prevent the effects of basic impurities and the like in an environmental atmosphere. These techniques may be employed in combination. The exposed resist film is then developed to form a specific resist pattern. As preferable examples of the developer used for development, alkaline aqueous solutions prepared by dissolving at least one of an alkaline compound such as sodium hydroxide, potassium hydroxide, sodium carbonate, sodium silicate, sodium metasilicate, aqueous ammonia, ethylamine, n-propylamine, diethylamine, di-n-propylamine, triethylamine, methyldiethylamine, ethyldimethylamine, triethanolamine, tetramethylammonium hydroxide, pyrrole, piperidine, choline, 1,8-diazabicyclo-[5.4.0]-7-undecene, and 1,5-diazabicyclo-[4.3.0]-5-nonene are given. The concentration of the alkaline aqueous solution is usually 10 wt % or less. If the concentration of the alkaline aqueous solution exceeds 10 wt %, an unexposed area may also be dissolved in the developer.

Organic solvents or the like may be added to the developer containing the alkaline aqueous solution. As examples of the organic solvents, ketones such as acetone, methyl ethyl ketone, methyl-1-butyl ketone, cyclopentanone, cyclohexanone, 3-methylcyclopentanone, and 2,6-dimethylcyclohexanone; alcohols such as methyl alcohol, ethyl alcohol, n-propyl alcohol, i-propyl alcohol, n-butyl alcohol, t-butyl alcohol, cyclopentanol, cyclohexanol, 1,4-hexanediol, and 1,4-hexanedimethylol; ethers such as tetrahydrofuran and dioxane; esters such as ethyl acetate, n-butyl acetate, and i-amyl acetate; aromatic hydrocarbons such as toluene and xylene; phenol, acetonyl acetone, dimethylformamide, and the like can be given. These organic solvents may be used either individually or in combination of two or more. The amount of the organic solvent to be used is preferably 100 vol % or less of the alkaline aqueous solution. The amount of the organic solvent exceeding 100 vol % may decrease developability, giving rise to a larger undeveloped portion in the exposed area. In addition, surfactants or the like may be added to the developer containing the alkaline aqueous solution in an appropriate amount. After development using the alkaline aqueous solution developer, the resist film is usually washed with water and dried.

When the polymer of the present invention is used as the resin component of the resin composition for forming an upper layer film, a solvent exhibiting almost no adverse effect on the lithographic performance by intermixing and the like with the photoresist film when applied onto the photoresist film can be preferably used.

Solvents containing a monohydric alcohol can be given as examples of the solvents. Examples of the monohydric alcohols include methanol, ethanol, 1-propanol, isopropanol, n-propanol, n-butanol, 2-butanol, t-butanol, 1-pentanol, 2-pentanol, 3-pentanol, n-hexanol, cyclohexanol, 2-methyl-2-butanol, 3-methyl-2-butanol, 2-methyl-1-butanol, 3-methyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 2,2-dimethyl-3-pentanol, 2,3-dimethyl-3-pentanol, 2,4-dimethyl-3-pentanol, 4,4-dimethyl-2-pentanol, 3-ethyl-3-pentanol, 1-heptanol, 2-heptanol, 3-heptanol, 2-methyl-2-hexanol, 2-methyl-3-hexanol, 5-methyl-1-hexanol, 5-methyl-2-hexanol, 2-ethyl-1-hexanol, 4-methyl-3-heptanol, 6-methyl-2-heptanol, 1-octanol, 2-octanol, 3-octanol, 2-propyl-1-pentanol, 2,4,4-trimethyl-1-pentanol, 2,6-dimethyl-4-heptanol, 3-ethyl-2,2-dimethyl-pentanol, 1-nonanol, 2-nonanol, 3,5,5-trimethyl-1-hexanol, 1-decanol, 2-decanol, 4-decanol, 3,7-dimethyl-1-octanol, and 3,7-dimethyl-3-octanol.

Of these monohydric alcohols, monohydric alcohols having 4 to 8 carbon atoms are preferable, with n-butanol and 4-methyl-2-pentanol being more preferable.

Other solvents may be added to adjust applicability when applying the upper layer film onto the photoresist film. The other solvents enable uniform application of the upper layer film without corroding the photoresist film.

As examples of the other solvents, polyhydric alcohols such as ethylene glycol and propylene glycol; cyclic ethers such as tetrahydrofuran and dioxane; alkyl ethers of polyhydric alcohol such as ethylene glycol monomethyl ether, ethylene glycol monoethyl ether, ethylene glycol dimethyl ether, ethylene glycol diethyl ether, diethylene glycol monomethyl ether, diethylene glycol monoethyl ether, diethylene glycol dimethyl ether, diethylene glycol diethyl ether, diethylene glycol ethyl methyl ether, propylene glycol monomethyl ether, and propylene glycol monoethyl ether; alkyl ether acetates of polyhydric alcohol such as ethylene glycol ethyl ether acetate, diethylene glycol ethyl ether acetate, propylene glycol ethyl ether acetate, and propylene glycol monomethyl ether acetate; aromatic hydrocarbons such as toluene and xylene; ketones such as acetone, methyl ethyl ketone, methyl isobutyl ketone, cyclohexanone, 4-hydroxy-4-methyl-2-pentanone, and diacetone alcohol; esters such as ethyl acetate, butyl acetate, ethyl-2-hydroxypropionate, methyl-2-hydroxy-2-methylpropionate, ethyl-2-hydroxy-2-methylpropionate, ethoxy ethyl acetate, hydroxy ethyl acetate, methyl-2-hydroxy-3-methylbutanate, methyl-3-methoxypropionate, ethyl-3-methoxypropionate, ethyl-3-ethoxypropionate, and methyl-3-ethoxypropionate, and water can be given. Of these, cyclic ethers, alkyl ethers of polyhydric alcohol, alkyl ether acetates of polyhydric alcohol, ketones, esters, and water are preferable.

The proportion of the other solvents to be added is 30 wt % or less, and preferably 20 wt % or less of the total amount of the solvent used. If more than 30 wt %, the photoresist film may be corroded and may cause intermixing with the upper layer film, leading to significant deterioration of resolution performance of the photoresist.

A surfactant can be blended with the resin composition for forming an upper layer film of the present invention in order to increase applicability, defoamability, leveling properties, and the like.

As examples of the surfactants, fluorine-containing surfactants commercially available under the trade names of "BM-1000" and "BM-1100" (manufactured by BM CHEMIE Co., Ltd.), "MEGAFAC F142D", "MEGAFAC F172", "MEGAFAC F173", and "MEGAFAC F183" (manufactured by Dainippon Ink and Chemicals, Inc.), "Fluorad FC-135", "Fluorad FC-170C", "Fluorad FC-430", and "Fluorad FC-431 (manufactured by Sumitomo 3M), "Surflon S-112" "Surflon S-113", "Surflon S-131", "Surflon S-141", and "Surflon S-145" (manufactured by Asahi Glass Co., Ltd.), "SH-28PA", "SH-190", "SH-193", "SZ-6032", and "SF-8428" (manufactured by Dow Corning Toray Silicone), "NBX-15" (manufactured by NEOS Company Limited) and surfactants not containing fluorine commercially available under the trade name of "POLYFLOW No. 75" (manufactured by Kyoeisha Chemical Co., Ltd.) can be given.

The amount of surfactants to be added is preferably 5 parts by weight or less for 100 parts by weight of the alkali-soluble resin.

The resin composition for forming an upper layer film of the present invention is applied onto a photoresist film for forming patterns by exposure to radiation. Particularly, the composition may be used as a resin composition for liquid immersion lithography for forming an upper layer film. Below is an example when the composition is used for liquid immersion lithography for forming an upper layer film.

A silicon wafer, an aluminum-coated wafer, or the like may be used as the substrate on which the photoresist film is formed by applying the photoresist composition. In order to bring out the potential of the resist film to the maximum extent, an organic or inorganic antireflection film may be formed on the substrate as disclosed in JP-B-6-12452, for example.

The photoresist used is not particularly limited, and may be appropriately selected according to the purpose of the resist. As examples of the resist, a chemically-amplified positive-tone or negative-tone resist containing an acid generator can be given.

When the upper layer film of the present invention is used, a positive-tone resist is particularly preferable. In the case of the chemically-amplified positive-tone resist, the acid-dissociating organic group in the polymer dissociates by the action of the acid generated from the acid generator by exposure to radiation and produce a carboxyl group, for example. The acid increases the solubility of the resist in the irradiated part in an alkaline developer to the extent that the irradiated part is dissolved and removed by an alkaline developer to produce a positive tone resist pattern.

The upper layer film is formed on the photoresist film by using the above-mentioned resin composition. The upper layer film is formed by applying the resin composition for forming an upper layer film of the present invention on the photoresist film and usually baking the composition further. The upper layer film is formed in order to protect the photoresist film and to prevent pollution of the lens of a projection aligner due to elution of components of the resist from the photoresist film into the liquid.

In this instance, the closer the thickness of the upper layer film to an anisoploid of $\lambda/4$ m (wherein $\lambda$ is the wavelength of radiation and m is the refractive index of the upper layer film), the greater the antireflection effect on the upper side surface of the resist film. Therefore, it is preferable to bring the thickness of the upper layer film close to this value. In the present invention, either prebaking after the application of the resist solution or baking after the application of the solution of resin composition for forming an upper layer film may be omitted for simplification of the process.

The photoresist film is then developed using a developer and washed to form a desired resist pattern. In this case, it is not necessary to add a step of delaminating the upper layer film. The upper layer film can be completely removed during development or washing after the development.

EXAMPLES

The embodiment of the present invention will be described in more detail by way of Examples. However, these examples should not be construed as limiting the present invention. In the examples, "part" refers to "part by weight" unless otherwise indicated.

Measurements and evaluation in the Examples and Comparative Examples were carried out as follows.

(1) Mw

The Mw was measured by gel permeation chromatography (GPC) using GPC columns ("TSKgel α-2500" and "TSKgel α-M" manufactured by Tosoh Corp.) under the following conditions: flow rate: 1.0 ml/min., eluate: dimethylformamide obtained by dissolving 30 mmol/l of LiBr and 10 mmol/l of $H_3PO_4$, column temperature: 40° C., detector: "MALLS" (DAWN DSP, cell type: K5, laser wavelength: 632.8 nm, manufactured by Wyatt Technology Corporation).

(2) Sensitivity

In Examples and Comparative Examples, the compositions were spin-coated on the substrates having a film with a thickness of 77 nm of "ARC 29A" (manufactured by Nissan Chemical Industries, Ltd.) formed on the surface of an wafer and prebaked on a hot plate at 100° C. for 60 seconds to form a resist film with a thickness of 200 nm. The resist film was exposed through a mask pattern using a full field reduced projection exposure apparatus ("S306C" manufactured by Nikon Corporation, numerical aperture: 0.75). After performing PEB at 110° C. for 60 seconds, the resist film was developed at 25° C. for 60 seconds in a 2.38 wt % tetramethylammonium hydroxide aqueous solution, washed with water, and dried to form a positive-tone resist pattern. An optimum dose at which a 1:1 line-and-space pattern with a line width of 100 nm was formed through a 1:1 line-and-space mask with a size of 100 nm was taken as "sensitivity".

(3) Resolution

Minimum dimensions of the resist pattern resolved at the optimum dose were taken as the resolution.

(4) Line Edge Roughness (LER)

In the observation of a 100 nm 1L/1S pattern resolved at an optimum dose of exposure, the line width was measured at arbitrary points from above the pattern using SEM ("S9220" manufactured by Hitachi, Ltd.) and the fluctuation of the measurements was expressed by $3\sigma$.

(5) Depth of Focus (DOF)

A 100 nm line-and-space pattern (1L1S) was exposed at an optimum dose of radiation under conditions in which the depth of focus was offset at an interval of 0.05 μm in a range from −1.0 μm to +1.0 μm. The range (μm) in which the line width was from 90 nm (−10%) to 110 nm (+10%) was taken as depth of focus.

(6) Amount of Elusion (Amount of Elusion of Acid Generator and Acid Diffusion Controller)

A 30 cm×30 cm square silicone rubber sheet with a thickness of 1.0 mm (manufactured by Kureha Elastomer Co., Ltd.), of which the center was cut out into a form of a disk with a diameter of 11.3 cm was superposed on the center of an 8-inch silicon wafer which was previously treated with hexamethyldisilazane (HMDS) at 100° C. for 60 seconds using "CLEAN TRACK ACT8" (manufactured by Tokyo Electron, Ltd.). The circular area of the center of the silicone rubber sheet, from which a disk was cut out, was filled with 10 ml of ultra pure water using a 10 ml one-mark pipette. Next, an underlayer antireflection film with a thicknesses of 77 m ("ARC29A" manufactured by Bruwer Science) was formed on the silicon rubber sheet using CLEAN TRACK ACT8, and a wafer, on which a resist film with a thicknesses of 205 nm was formed by applying the resist compositions shown in Table 1 onto the underlayer antireflection film by spin coating using the CLEAN TRACK ACT8 and baking at 115° C. for 60 seconds, was superposed in such a manner that the resist coating surface could come in contact with the ultra pure water and the ultra pure water would not leak from the silicon rubber.

After 10 seconds, the 8-inch silicon wafer was removed, and the ultra-pure water was collected, utilizing a glass injector, for use as a sample for analysis. The recovery rate of the ultra-pure water after completion of the experiment was 95% or more.

The peak intensity of the anion part of the photoacid generator in the collected ultra-pure water was measured using LC-MS (a liquid chromatograph mass spectrometer, LC section: "SERIES1100" manufactured by AGILENT Corp., MS section: "Mariner" manufactured by Perseptive Biosystems, Inc.) under the following conditions. In this instance, peak intensities of the aqueous solutions of triphenylsulfonium nonafluoro-n-butane sulfonate at concentrations of 1 ppb, 10 ppb, and 100 ppb were measured under the above conditions to prepare a calibration curve. The eluted amount was calculated from the above peak intensity using this calibration curve. In the same manner, the peak intensities of aqueous solutions of the acid diffusion controller at concentrations of 1 ppb, 10 ppb, and 100 ppb were measured under the same conditions to prepare calibration curves. The eluted amount of the acid diffusion controller was calculated from the above peak intensity using these calibration curves.

(7) Liquid Immersion Exposure Intensity

A 12-inch silicon wafer on which an underlayer antireflection film with a thickness of 77 nm ("ARC29A" manufactured by Bruwer Science) had been formed was used as a substrate. "CLEAN TRACK ACT12" (manufactured by Tokyo Electron Ltd.) was used for preparing the underlayer antireflection film.

Resist coatings with a thickness of 150 nm were formed on the above-mentioned substrate by spin coating the resin compositions shown in Table 1 using CLEAN TRACK ACT 12 and baking under the conditions shown in Table 1. The resist coatings were exposed to radiation through a mask pattern using an ArF excimer laser exposure apparatus ("TWIN SCAN XT1250i" manufactured by ASML, lighting conditions: NA 0.85, σ 0.93/0.69). After PEB at 130° C. for 90 seconds, the resist coatings were developed at 23° C. for 30 seconds in a 2.38 wt % tetramethylammonium hydroxide aqueous solution, washed with pure water, and dried to form positive-tone resist patterns. An optimum exposure dose at which a 1:1 line-and-space pattern with a line width of 90 nm was formed through a 1:1 line-and-space mask with a size of 100 nm was taken as "sensitivity". The measurement was carried out using a scanning electron microscope ("S-9380" manufactured by Hitachi High-Technologies Corporation).

(8) Liquid Immersion Exposure Resolution

Minimum dimensions of the line- and space pattern resolved at the optimum exposure dose were taken as the resolution. The measurement was carried out using a scanning electron microscope ("S-9380" manufactured by Hitachi High-Technologies Corporation).

(9) Pattern Shape Formed by Liquid Immersion Exposure

A cross-sectional shape of 90 nm line-and-space patterns was observed using a scanning electron microscope ("S-4200" manufactured by Hitachi High-Technologies Corporation). FIG. 1 shows an example of a cross-sectional shape of the resist pattern.

In FIG. 1, a and b respectively indicate the line width at the top and bottom of the pattern shape. When $0.9 \leq a/b \leq 1.1$ was satisfied, the pattern shape was evaluated as "Good", otherwise the pattern shape was evaluated as "Bad". a and b were calculated by measuring the points shown in FIG. 1 and averaging ten arbitrary points on the wafer.

Example 1

A novel compound (M-1) as a monomer to obtain the polymer of the present invention was prepared by the following method. The synthesis process is as follows.

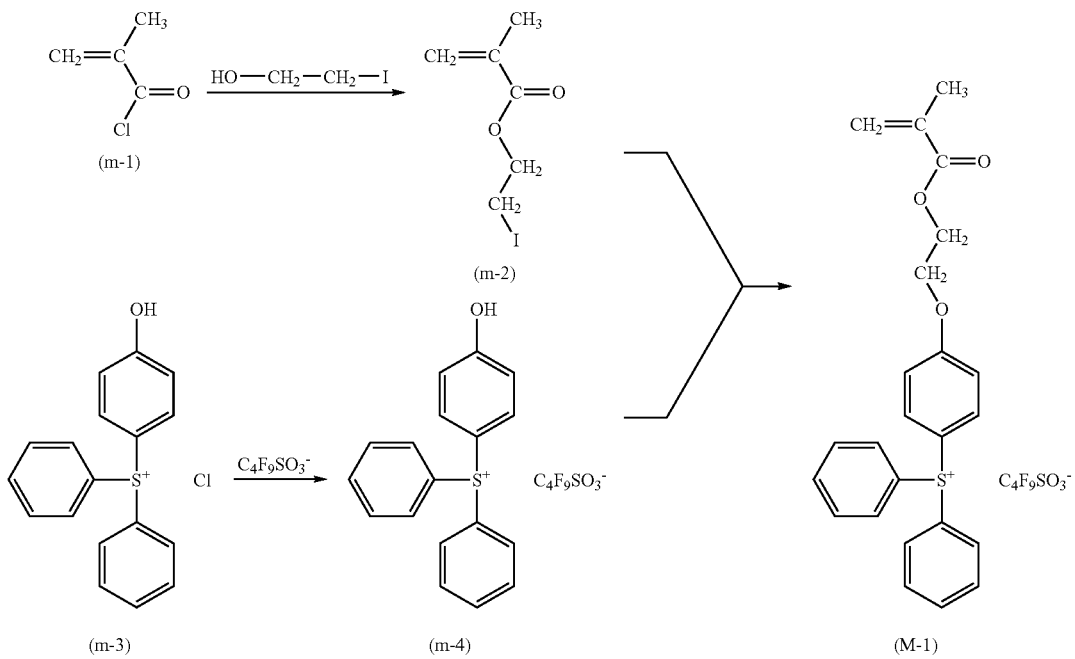

(a) Synthesis of compound (m-2)

Under a nitrogen atmosphere, a three-necked flask equipped with a stirrer chip and a dropping funnel was charged with 20.9 g (200 mmol) of the compound (m-1), which was dissolved in 160 ml of dichloromethane. The dichloromethane solution was cooled to 0° C. and 30.4 g (300 mmol) of triethylamine was added, followed by further stirring. After adding 37.8 g (220 mmol) of ethanol diiodide dropwise over 30 minutes, the reaction solution was heated to room temperature and stirred for two hours. After the reaction, the reaction solution was added to 300 ml of saturated ammonia chloride water and the dichloromethane layer was extracted using a separating funnel. The remaining water layer was extracted twice with 200 ml of dichloromethane. After removing the solvent from the collected dichloromethane layer, the residue was separated using column chromatography to obtain a compound (m-2).

(b) Synthesis of Compound (m-4)

A three-necked flask was charged with 5.0 g of the compound (m-3), 4.9 g of lithium nonafluorobutane sulfonate, 30 ml of ion-exchanged water, and 40 ml of chloroform, and the mixture was stirred for one hour. The organic layer was extracted from the reaction solution, the extract was washed three times with ion-exchanged water, and the organic solvent was removed to obtain a compound (m-4).

(c) Synthesis of Compound (M-1)

Under a nitrogen atmosphere, a three-necked flask equipped with a stirrer chip and a dropping funnel was charged with 9.3 g of the compound (m-4), 3.3 g of potassium carbonate, and 50 ml of dimethylformamide, and the mixture was stirred for 30 minutes. 4.2 g of the compound (m-2) was added to the reaction solution, the mixture was stirred at 80° C. for five hours and added to 150 ml of ion-exchanged water to extract organic layers three times with ethyl acetate. After the extracted solutions were washed three times with ion-exchanged water, the solvent was removed to obtain a compound (M-1) by column chromatography. Identification data of the compound (M-1) is as follows. Results of $^1$H NMR σ ppm (CDCl$_3$): 1.94 (3H, dd), 4.28-4.56 (4H, m), 5.60 (1H, dt), 6.12 (1H, dt), 7.63-7.95 (14H, Ph)

Results of LC-MS positive: 391, negative: 299

Example 2

A compound (M-2) was prepared in the same manner as in Example 1. Identification data of the compound (M-2) is as follows.

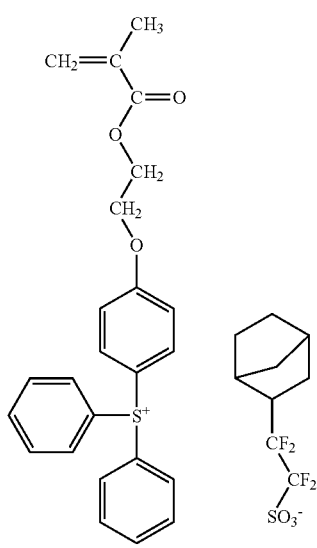

(M-2)

Results of $^1$H NMR σ0 ppm (CDCl$_3$): 1.23-2.78 (14H, m), 4.27-4.54 (4H, m), 5.59 (1H, dt), 6.10 (1H, dt), 7.23-7.88 (14H, Ph)

Results of LC-MS positive: 391, negative: 275

Example 3

A compound (M-3) was prepared in the same manner as in Example 1. Identification data of the compound (M-3) is as follows.

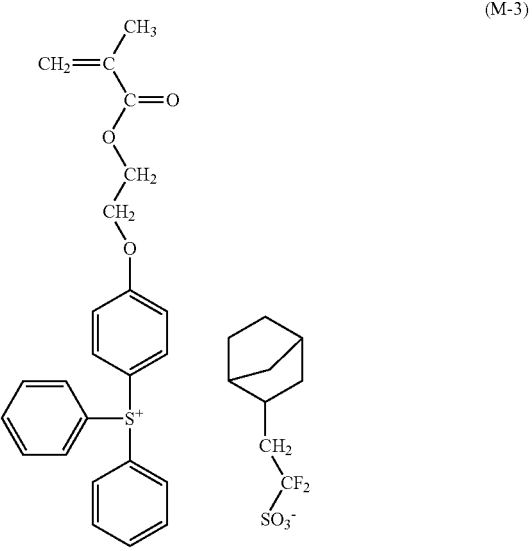

(M-3)

Results of $^1$H NMR σ ppm (CDCl$_3$): 0.80-2.47 (16H, m), 4.28-4.53 (4H, m), 5.60 (1H, dt), 6.13 (1H, dt), 7.20-7.84 (14H, Ph)

Results of LC-MS positive: 391, negative: 239

Synthesis of Polymer

Polymers were synthesized by using the compounds (M-1), (M-2), and (M-3) obtained in Examples and the following compounds (M-4) to (M-11). The compounds (M-4) to (M-9) are monomers which generate repeating units having an acid-dissociable group and the compounds (M-10) and (M-11) are monomers which generate other repeating units.

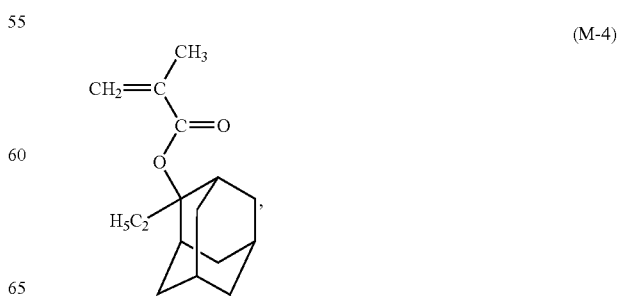

(M-4)

-continued

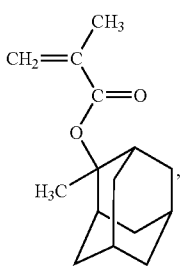 (M-5)

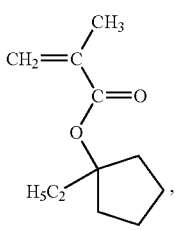 (M-6)

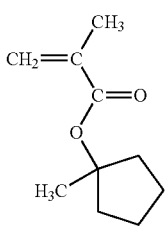 (M-7)

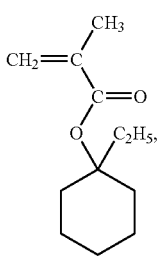 (M-8)

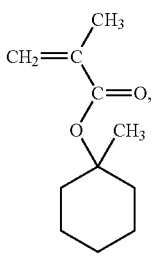 (M-9)

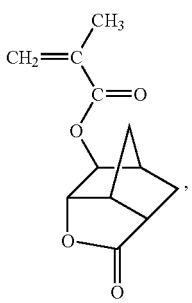 (M-10)

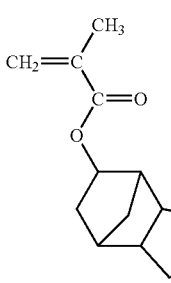 (M-11)

Example 4

A monomer solution was prepared by dissolving 7.80 g (51 mol %) of the compound (M-10), 5.77 g (46 mol %) of the compound (M-6), and 1.43 g (3 mol %) of the compound (M-1) in 30 g of 2-butanon, and further adding 0.23 g of azobis isobutylonitrile. A 100 ml three-necked flask containing 15 g of 2-butanone was purged with nitrogen for 30 minutes. After the nitrogen purge, the flask was heated to 80° C. while stirring, and the above monomer solution was added dropwise using a dropping funnel over three hours. The polymerization reaction was carried out for six hours after initiation of the addition. After completion of polymerization, the polymer solution was cooled with water to 30° C. or lower and poured into 300 g of isopropanol. A white powder deposited was collected by filtration.

The white powder was washed twice with 50 g of isopropanol in the form of a slurry and filtered. The filtrate was dried at 60° C. for 17 hours under vacuum to obtain a white powdery polymer (10.9 g; yield: 72.7 wt %). The polymer was a copolymer with an Mw of 13,000, an Mw/Mn ratio of 1.9, and the content of the repeating units of the compound (M-10), the compound (M-6), and the compound (M-1) determined by $^{13}$C-NMR was 48:49:3 (mol %). This copolymer is referred to as a polymer (A-1).

Example 5

Polymers (A-2) to (A-10) having the following contents of the repeating units (mol %) were synthesized in the same manner as in Example 4.

Polymer (A-2):
(M-10)/(M-5)/(M-6)/(M-1)=48/34/15/3, Mw=13,000, Mw/Mn=1.9

Polymer (A-3):
(M-10)/(M-11)/(M-6)/(M-1)=48/10/39/3, Mw=12,000, Mw/Mn=1.8

Polymer (A-4):
(M-10)/(M-7)/(M-1)=48/49/3, Mw=11,000, Mw/Mn=1.7

Polymer (A-5):
(M-10)/(M-4)/(M-8)/(M-1)=48/34/15/3, Mw=8,000, Mw/Mn=1.7

Polymer (A-6):
(M-10)/(M-5)/(M-9)/(M-1)=48/34/15/3, Mw=14,000, Mw/Mn=2.0

Polymer (A-7):
(M-10)/(M-5)/(M-6)/(M-2)=48/34/15/3, Mw=12,000, Mw/Mn=1.8

Polymer (A-8):

(M-10)/(M-11)/(M-6)/(M-2)=48/10/39/3, Mw=13,000, Mw/Mn=1.9
Polymer (A-9):
(M-10)/(M-5)/(M-6)/(M-3)=48/15/34/3, Mw=11,000, Mw/Mn=1.7
Polymer (A-10):
(M-10)/(M-11)/(M-6)/(M-3)=48/10/39/3, Mw=15,000, Mw/Mn=2.1

Comparative Example 1

Polymers (R-1) and (R-2) having the following contents of the repeating units (mol %) and not containing the compounds (M-1) to (M-3) were synthesized in the same manner as in Example 4.
Polymer (R-1):
(M-10)/(M-5)/(M-6)=50/36/14, Mw=8,000, Mw/Mn=1.7
Polymer (R-2):
(M-10)/(M-6)=51.2/48.8, Mw=8,000, Mw/Mn=1.7

Examples 6 to 18 and Comparative Example 2

The resin compositions containing the polymers prepared in Examples and Comparative Examples as the resin components and the components shown in Table 1 were evaluated. The evaluation results are shown in Table 2. In Table 1, components other than the resins are as follows.
Acid generator (B)
B-1: triphenylsulfonium nonafluoro-n-butanesulfonate
Acid diffusion controller (D)
D-1: 3-pyperidino-1,2-propanediol
D-2: N-t-butoxycarbonyl-4-hydroxypiperidine
D-3: 2,6-diisopropylaniline
Solvent (C)
C-1: propylene glycol monomethyl ether acetate
C-2: 2-heptanone
C-3: cyclohexanone

TABLE 1

| | Resin (part) | Acid generator (B) | Acid diffusion controller (D) (part) | Solvent (C) (part) |
|---|---|---|---|---|
| Example | | | | |
| 6 | A-1(100) | — | D-3(0.20) | C-1(650) C-2(200) |
| 7 | A-2(100) | — | D-2(0.20) | C-1(650) C-2(200) |
| 8 | A-3(100) | — | D-3(0.20) | C-1(650) C-2(200) |
| 9 | A-4(100) | — | D-1(0.20) | C-1(650) C-2(200) |
| 10 | A-5(100) | — | D-2(0.20) | C-1(650) C-3(200) |
| 11 | A-6(100) | — | D-2(0.20) | C-1(650) C-3(200) |
| 12 | A-1(50) R-1(50) | — | D-2(0.20) | C-1(650) C-3(200) |
| 13 | A-1(50) R-2(50) | B-1(1) | D-3(0.20) | C-1(650) C-3(200) |
| 14 | A-1(100) | B-1(1) | D-2(0.30) | C-1(650) C-3(200) |
| 15 | A-7(100) | — | D-3(0.20) | C-1(650) C-2(200) |
| 16 | A-8(100) | — | D-1(0.20) | C-1(650) C-2(200) |
| 17 | A-9(100) | — | D-2(0.20) | C-1(650) C-3(200) |
| 18 | A-10(100) | — | D-2(0.20) | C-1(650) C-3(200) |
| Comparative example | | | | |
| 2 | R-1(100) | B-1(4) | D-2(0.20) | C-1(450) C-3(200) |

TABLE 2

| | Sensitivity (J/m$^2$) | Resolution (nm) | DOF (µm) | LER (nm) | Sensitivity (liquid immersion) (J/m$^2$) | Resolution (liquid immersion exposure) (nm) | Elusion of acid generator (ppb) | Pattern shape formed by liquid immersion exposure |
|---|---|---|---|---|---|---|---|---|
| Example | | | | | | | | |
| 6 | 260 | 90 | 0.7 | 4.4 | 140 | 85 | Not detected | 0.9 (Good) |
| 7 | 270 | 90 | 0.6 | 4.5 | 160 | 85 | Not detected | 1.0 (Good) |
| 8 | 240 | 90 | 0.7 | 4.3 | 150 | 85 | Not detected | 1.0 (Good) |
| 9 | 240 | 90 | 0.6 | 4.5 | 160 | 85 | Not detected | 0.9 (Good) |
| 10 | 260 | 90 | 0.6 | 4.3 | 140 | 85 | Not detected | 1.1 (Good) |
| 11 | 240 | 90 | 0.7 | 4.6 | 150 | 85 | Not detected | 1.0 (Good) |
| 12 | 280 | 90 | 0.7 | 4.5 | 160 | 85 | Not detected | 1.0 (Good) |
| 13 | 260 | 90 | 0.7 | 4.5 | 170 | 85 | Not detected | 1.1 (Good) |
| 14 | 260 | 90 | 0.6 | 4.6 | 170 | 85 | Not detected | 0.9 (Good) |
| 15 | 240 | 90 | 0.7 | 4.1 | 160 | 85 | Not detected | 1.0 (Good) |
| 16 | 250 | 90 | 0.6 | 4.2 | 160 | 85 | Not detected | 1.0 (Good) |
| 17 | 260 | 90 | 0.6 | 4 | 180 | 85 | Not detected | 0.9 (Good) |
| 18 | 240 | 90 | 0.7 | 3.9 | 140 | 85 | Not detected | 0.9 (Good) |
| Comparative example | | | | | | | | |
| 2 | 280 | 100 | 0.4 | 7.4 | 190 | 95 | 425 | 1.2 (Bad) |

INDUSTRIAL APPLICABILITY

The radiation-sensitive resin composition of the present invention is useful as a chemically-amplified resist responsive to an active ray, for example deep ultraviolet rays such as a KrF excimer laser (wavelength: 248 nm) and an ArF excimer laser (wavelength: 193 nm). Since the resist has a high resolution and, in particular, has a wide DOF and excellent LER, the resin composition is highly suitable for fabrication of integrated circuit devices that are expected to become more and more miniaturized in the future.

BRIEF DESCRIPTION OF THE DRAWINGS

FIG. 1 is a cross-sectional view of the resist pattern.
Explanation of Symbols
a: Top width of the pattern shape
b: Bottom width of the pattern shape

The invention claimed is:

1. A polymer comprising a first repeating unit derived from a compound shown by the following formula (1),

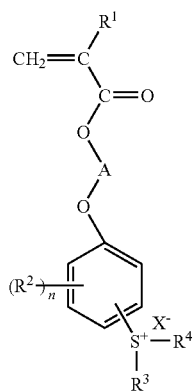

(1)

wherein $R^1$ represents a methyl group or a hydrogen atom, $R^2$ individually represents a substituted or unsubstituted monovalent organic group having 1 to 10 carbon atoms, n is an integer from 0 to 3, $R^3$ and $R^4$ individually represent a substituted or unsubstituted monovalent aryl group, A represents a methylene group, a linear or branched alkylene group having 2 to 10 carbon atoms, or an arylene group, and $X^-$ represents a sulfonate ion, a $BF^{4-}$ ion, a $PF^{6-}$ ion, or a tetraarylboronium ion, and a second repeating unit having an acid-dissociable group, and wherein the polymer has a polystyrene-reduced weight average molecular weight measured by gel permeation chromatography (GPC) of 1,000 to 100,000.

2. A polymer according to claim 1, wherein the substituted or unsubstituted monovalent aryl group is a phenyl group.

3. A polymer according to claim 1, wherein the $X^-$ is the sulfonate ion.

4. A radiation-sensitive resin composition comprising a resin containing an acid-dissociable group which is insoluble or scarcely-soluble in alkali and becomes readily-soluble in alkali by the action of an acid, wherein the resin containing an acid-dissociable group is the polymer according to claim 1.

5. A radiation-sensitive resin composition for liquid immersion lithography used in a system or a method of liquid immersion lithography which comprises irradiation through a liquid between a lens and a photoresist film, wherein the radiation-sensitive resin composition is applied onto the photoresist film to form an upper layer film covering the photoresist film, and wherein the radiation-sensitive resin composition is the resin composition according to claim 4.

* * * * *